(12) United States Patent
Takata

(10) Patent No.: US 12,213,225 B2
(45) Date of Patent: Jan. 28, 2025

(54) CONTROL DEVICE AND CONTROL METHOD

(71) Applicant: OLYMPUS CORPORATION, Tokyo (JP)

(72) Inventor: Yuhei Takata, Mitaka (JP)

(73) Assignee: Olympus Corporation, Tokyo (JP)

( * ) Notice: Subject to any disclaimer, the term of this patent is extended or adjusted under 35 U.S.C. 154(b) by 148 days.

(21) Appl. No.: 18/115,532

(22) Filed: Feb. 28, 2023

(65) Prior Publication Data

US 2023/0284356 A1   Sep. 7, 2023

Related U.S. Application Data

(60) Provisional application No. 63/315,421, filed on Mar. 1, 2022.

(51) Int. Cl.
*H05B 47/105*   (2020.01)
*A61B 18/00*   (2006.01)
*A61B 18/24*   (2006.01)
*A61B 18/20*   (2006.01)

(52) U.S. Cl.
CPC ......... *H05B 47/105* (2020.01); *A61B 18/245* (2013.01); *A61B 2018/00505* (2013.01); *A61B 2018/00732* (2013.01); *A61B 2018/00982* (2013.01); *A61B 2018/2025* (2013.01)

(58) Field of Classification Search
None
See application file for complete search history.

(56) References Cited

U.S. PATENT DOCUMENTS

| | | | |
|---|---|---|---|
| 2017/0059849 A1* | 3/2017 | Daidoji | A61B 1/07 |
| 2017/0232269 A1* | 8/2017 | Luttrull | A61N 2/02 |
| | | | 601/3 |
| 2017/0354464 A1 | 12/2017 | Waisman et al. | |
| 2018/0228424 A1* | 8/2018 | Hong | A61B 5/418 |
| 2019/0117055 A1* | 4/2019 | Ito | G02B 23/2461 |
| 2021/0271061 A1* | 9/2021 | Fukazawa | A61B 1/045 |
| 2021/0278658 A1* | 9/2021 | Ito | A61B 1/07 |
| 2021/0378745 A1 | 12/2021 | Fukushima et al. | |
| 2021/0402209 A1* | 12/2021 | Kim | A61N 5/0616 |
| 2022/0370118 A1* | 11/2022 | Won | A61B 17/320092 |

FOREIGN PATENT DOCUMENTS

WO   2020/174686 A1   9/2020

* cited by examiner

*Primary Examiner* — Wilson Lee
(74) *Attorney, Agent, or Firm* — Morgan, Lewis & Bockius LLP

(57) ABSTRACT

A control device, comprising: a processor including hardware, the processor being configured to: control a laser light source to emit a first instance of a laser light, calculate an overlap information related to an overlap area of an irradiation area of an irradiation target that is irradiated with the first instance of the laser light, and control the laser light source to emit a second instance of the laser light based on the overlap information.

20 Claims, 8 Drawing Sheets

CONTROL DEVICE AND CONTROL METHOD

CROSS-REFERENCE TO RELATED APPLICATION

This application is based on and claims priority under 35 U.S.C. § 119 to U.S. Provisional Application No. 63/315,421, filed on Mar. 1, 2022, the entire contents of which are incorporated herein by reference.

BACKGROUND

1. Technical Field

The present disclosure relates to a control device and a control method.

2. Related Art

In the related art, a technology is known that causes a laser light source to emit a pulse of laser light and irradiates a calculus as a crushing target with the laser light through an optical fiber to crush the calculus.

In a technology described in US 2017/0354464 A, a quantity of laser light that is reflected by and returned from a calculus is used to measure a distance to the calculus, determining a condition of the laser light on the basis of the distance.

SUMMARY

In some embodiments, a control device, comprising: a processor including hardware, the processor being configured to: control a laser light source to emit a first instance of a laser light, calculate an overlap information related to an overlap area of an irradiation area of an irradiation target that is irradiated with the first instance of the laser light, and control the laser light source to emit a second instance of the laser light based on the overlap information.

In some embodiments, a control device, comprising:
a processor including hardware, the processor being configured to: control operation of a laser light source to cause the laser light source to emit a pulse of laser light and to apply the laser light to an irradiation target through an optical fiber, calculate a scanning speed according to a movement of the optical fiber relative to the irradiation target, and control an output of the laser light from the laser light source based on the scanning speed.

In some embodiments, provided is a control method executed by a processor of a control device, the control method comprising: calculating an overlap information related to an overlap area of a first irradiation area of an irradiation target that is irradiated with a first instance of a laser light emitted from a laser light source, and controlling the laser light source to emit a second instance of the laser light based on the overlap information.

The above and other features, advantages and technical and industrial significance of this disclosure will be better understood by reading the following detailed description of presently embodiments of the disclosure, when considered in connection with the accompanying drawings.

DETAILED DESCRIPTION

Figure 1:
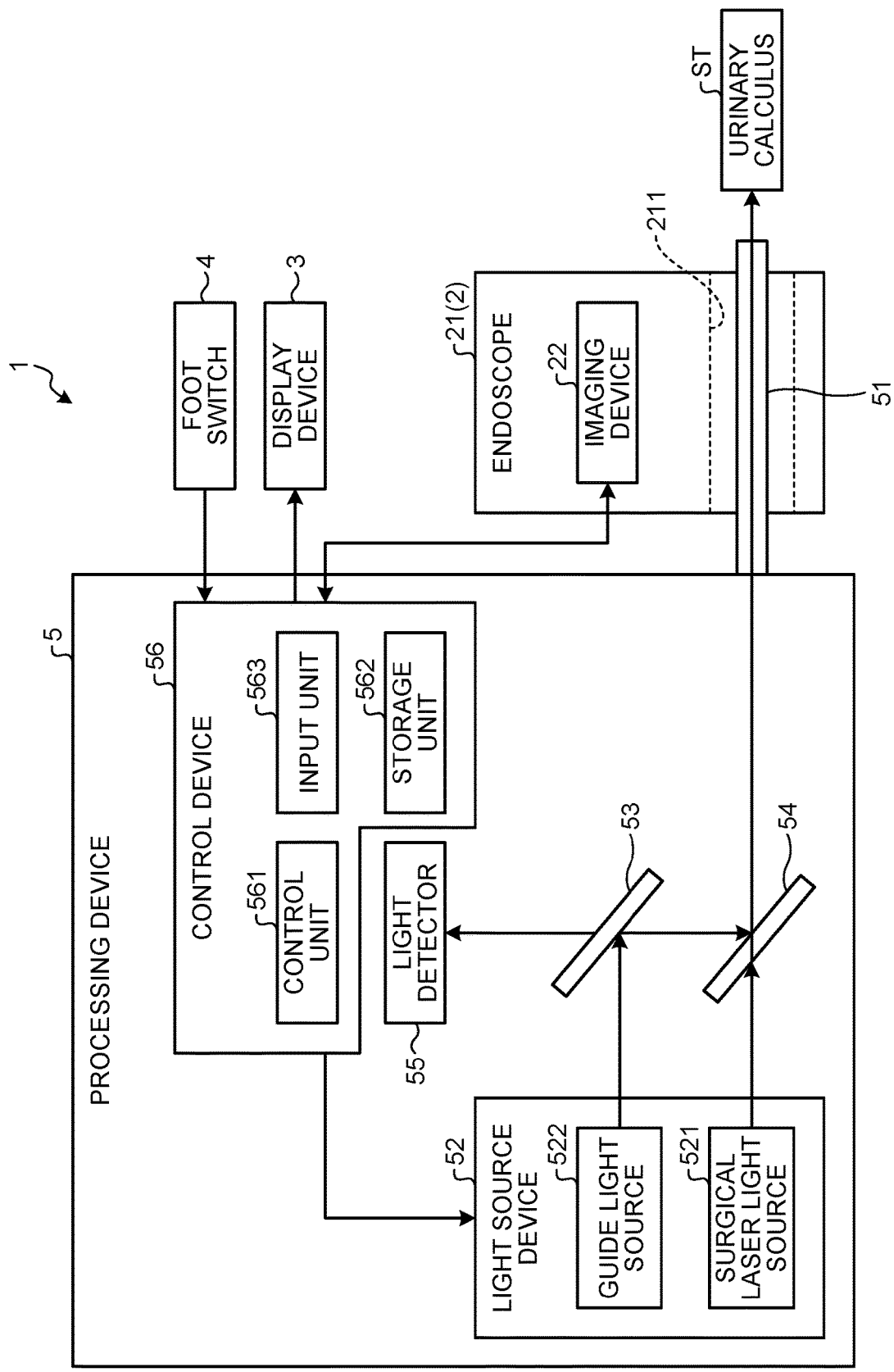
FIG. 1 is a block diagram illustrating a configuration of a surgical system according to a first embodiment.

Modes for carrying out the disclosure (hereinafter referred to as "embodiments") will be described below with reference to the drawings. It should be understood that the disclosure is not limited to the embodiments described below. Furthermore, in the description of the drawings, the same portions are denoted by the same reference numerals and symbols.

First Embodiment

Configuration of Surgical System

FIG. 1 is a block diagram illustrating a configuration of a surgical system 1 according to a first embodiment.

The surgical system 1 is a system that crushes an irradiation target (urinary calculus ST (FIG. 1) in the present first embodiment) in a living body with laser light while observing the inside of the living body. As illustrated in FIG. 1, the surgical system 1 includes an endoscope 2, a display device 3, a foot switch 4, and a processing device 5.

The endoscope 2 is partially inserted into a living body, images inside the living body, and outputs an image signal (hereinafter, referred to as endoscopic image) generated by the imaging. As illustrated in FIG. 1, the endoscope 2 includes an insertion section 21 and an imaging device 22.

The insertion section 21 is a portion at least part of which has flexibility and that is inserted into a living body. In the insertion section 21, a channel 211 is provided that longitudinally penetrates the insertion section 21.

The imaging device 22 is provided at a distal end portion in the insertion section 21. The imaging device 22 includes an imaging element such as a charge coupled device (CCD) or a complementary metal oxide semiconductor (CMOS) that receives a subject image and converts the subject image into an electric signal, and outputs the endoscopic image generated by imaging inside the living body to the processing device 5.

The display device 3 is a liquid crystal display (LCD), an electro luminescence (EL) display, or the like, and displays the endoscopic image or the like under the control of the processing device 5.

The foot switch 4 receives a start operation for starting crushing of the urinary calculus ST. Then, the foot switch 4 outputs a signal according to the start operation to the processing device 5

Note that a configuration for receiving the start operation is not limited to the foot switch 4 operated by an operator's foot, and a switch or the like operated by a hand may be adopted.

As illustrated in FIG. 1, the processing device 5 includes an optical fiber 51, a light source device 52, a half mirror 53, a dichroic mirror 54, a light detector 55, and a control device 56.

As illustrated in FIG. 1, the optical fiber 51 is inserted into the channel 211 of the insertion section 21. Note that in the present first embodiment, the number of the optical fibers 51 is one as illustrated in FIG. 1, but the number of the optical fibers 51 is not limited to one and may be two or more.

Under the control of the control device 56, the light source device 52 emits surgical laser light used for crushing the urinary calculus ST, and guide light. As illustrated in FIG. 1, the light source device 52 includes a surgical laser light source 521 and a guide light source 522.

The surgical laser light source 521 corresponds to a laser light source, and emits a pulse of surgical laser light. Examples of the surgical laser light source 521 include a semiconductor laser that emits surgical laser light in a mid-infrared wavelength band of approximately 2 µm, and the like.

The guide light source 522 emits guide light. Examples of the guide light source 522 includes a light emitting diode (LED) that emits guide light in a visible wavelength band or an LED that emits guide light in a near-infrared wavelength band, a semiconductor laser, and the like. For example, if the guide light source 522 includes a green LED that emits guide light in a green wavelength band and a red LED that emits guide light in a red wavelength band, the color of the guide light can be changed to green or red under the control of the control device 56.

Then, the guide light emitted from the guide light source 522 travels in the same direction as that of the surgical laser light so as to be parallel to the surgical laser light emitted from the surgical laser light source 521, as indicated by an arrow in FIG. 1.

The half mirror 53 reflects part of the guide light emitted from the guide light source 522 and causes the reflected guide light to travel toward the dichroic mirror 54.

The dichroic mirror 54 reflects light in a wavelength band of the guide light and transmits light in a wavelength band of the surgical laser light.

Here, the guide light emitted from the guide light source 522, passing through the half mirror 53, and then reflected by the dichroic mirror 54 travels on the same optical axis as that of the surgical laser light transmitted through the dichroic mirror 54, and enters a proximal end of the optical fiber 51. The guide light entering the proximal end of the optical fiber 51 is propagated through the optical fiber 51, emitted from a distal end of the optical fiber 51, and applied to the urinary calculus ST to form a spot of the guide light at an irradiation position on the urinary calculus. At this time, the operator can recognize the spot of the guide light on the basis of the endoscopic image displayed on the display device 3. Note that the spot corresponds to the irradiation position on the urinary calculus ST to which the surgical laser light is applied.

Furthermore part of the guide light (hereinafter, referred to as feedback light) applied to the urinary calculus ST and reflected from the urinary calculus ST enters the distal end of the optical fiber 51. The feedback light having entered the distal end of the optical fiber 51 is propagated through the optical fiber 51, passes through the dichroic mirror 54 and the half mirror 53 from the proximal end of the optical fiber 51, and then enters the light detector 55.

Meanwhile, the surgical laser light emitted from the surgical laser light source 521 and transmitted through the dichroic mirror 54 passes through the optical fiber 51, and then is emitted from the distal end of the optical fiber 51 and applied to the urinary calculus ST, as in the guide light described above. Then, the surgical laser light is emitted from the distal end of the optical fiber 51 to the urinary calculus ST, and the urinary calculus ST is crushed.

The light detector 55 detects the feedback light and outputs a signal according to a result of the detection to the control device 56.

The control device 56 collectively controls the operations of the entire surgical system 1. As illustrated in FIG. 1, the control device 56 includes a control unit 561, a storage unit 562, and an input unit 563.

The control unit 561 corresponds to a processor. The control unit 561 includes a controller such as a central processing unit (CPU) or micro processing unit (MPU), or an integrated circuit such as an application specific integrated circuit (ASIC) or field programmable gate array (FPGA), and controls the operations of the entire surgical system 1. Note that the functions of the control unit 561 will be described in a "control method" which is described later.

The storage unit 562 stores various programs (including a control program) executed by the control unit 561, information necessary for processing by the control unit 561, and the like. Here, examples of the information necessary for processing by the control unit 561 can include data such as a pulse frequency f of pulses of surgical laser light emitted, a fiber diameter D of the optical fiber 51, a numerical aperture NA of the optical fiber 51, and a refractive index n (approximately 1.3) of a medium (saline solution) through which the surgical laser light passes. Note that the pulse frequency f may be configured to be changeable to a value depending on the preference of the operator, according to a user operation to the input unit 563 by the operator or the like.

The input unit 563 includes a keyboard, a mouse, a switch, a touch panel, or the like, and receives the user operation by the operator or the like. Then, the input unit 563 outputs a scanning signal according to the user operation, to the control unit 561.

Control Method

Next, the control method executed by the control device 56 will be described.

Figure 2:
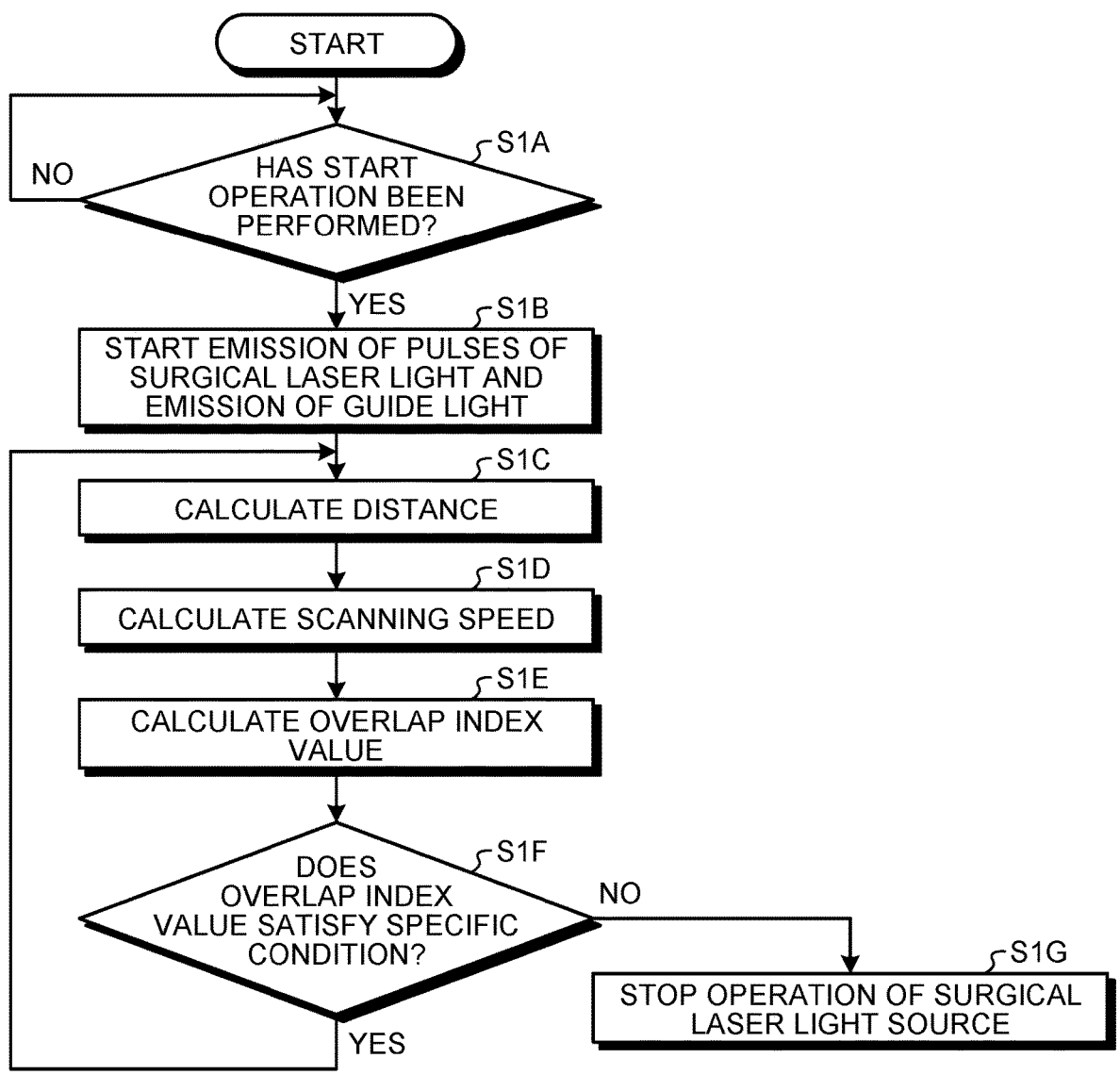
FIG. 2 is a flowchart illustrating a control method executed by a control device.
Figure 3:
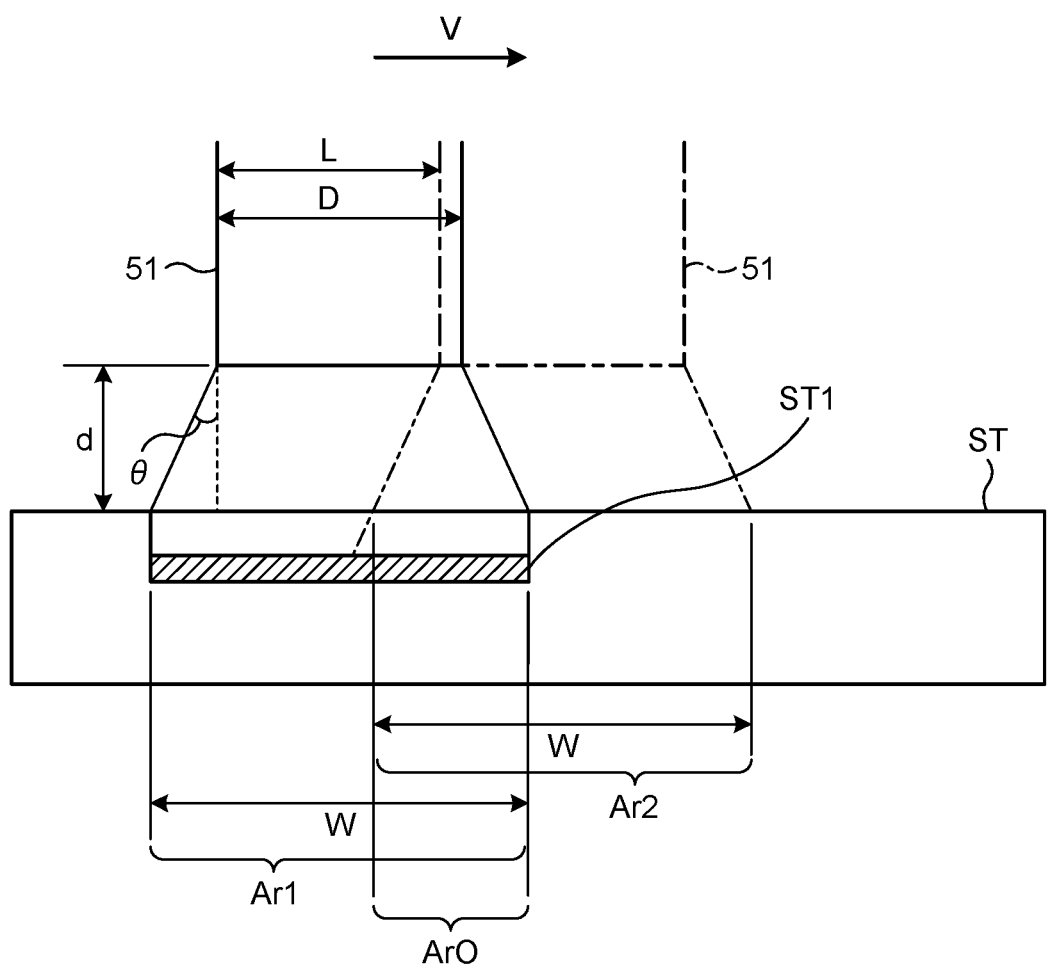
FIG. 3 is a diagram illustrating the control method.

FIG. 2 is a flowchart illustrating the control method executed by the control device 56. FIG. 3 is a diagram illustrating the control method. Specifically, FIG. 3 illustrates a state in which the surgical laser light is applied to the urinary calculus ST through the optical fiber 51. Note that, in FIG. 3, a solid line indicates the optical fiber 51 and the surgical laser light upon emission of a pulse of the surgical laser light (hereinafter, described as first pulse emission) at predetermined timing. Meanwhile, in FIG. 3, an alternate long and short dash line indicates the optical fiber 51 and the surgical laser light upon emission of a pulse of the surgical laser light (hereinafter, described as second pulse emission) at timing immediately after the first pulse emission.

First, the control unit 561 constantly monitors whether the start operation is input to the foot switch 4 by the operator (Step S1A).

Then, when it is determined that the start operation has been input (Step S1A: Yes), the control unit 561 controls the operation of the light source device 52 to cause the surgical laser light source 521 to start emission of pulses of the surgical laser light and cause the guide light source 522 to start emission of the guide light (Step S1B).

After Step S1B, the control unit 561 calculates a distance d (FIG. 3) between the distal end of the optical fiber 51 and the urinary calculus ST (Step S1C).

Specifically, as a calculation method for calculating the distance d, any one of the following calculation methods (1) to (3) can be adopted.

(1) Calculation Method for Calculating Distance d Based on Brightness of Feedback Light The control unit 561 calculates the distance d on the basis of the brightness of the feedback light detected by the light detector 55. Specifically, there is a correlation between the distance d and the brightness of the feedback light. For example, as the distance d decreases, the brightness of the feedback light increases. Then, the control unit 561 refers to, for example, data indicating the correlation, stored in the storage unit 562, and calculates the distance d corresponding to the brightness of the feedback light detected by the light detector 55.

(2) Calculation Method for Calculating Distance d Based on Time-of-Flight Method The control unit 561 causes the guide light source 522 to emit a pulse of the guide light, and calculates the distance d on the basis of a time from emission of the pulse of the guide light to detection of the feedback light by the light detector 55. In other words, the control unit 561 calculates the distance d by using the so-called time-of-flight method.

(3) Calculation Method for Calculating Distance d Based on Endoscopic Image

The control unit 561 calculates the distance d on the basis of the endoscopic image obtained by imaging the urinary calculus ST.

Specifically, for example, the imaging device 22 includes a stereo camera. The control unit 561 calculates the distance d by using a stereo measurement technology in which a relative displacement in images of the same object that are imaged at the same time from different viewpoints by the stereo camera to calculate a three-dimensional position of the object on the basis of the principle of triangulation.

Furthermore, for example, the imaging device 22 includes a range image sensor such as a time of flight (TOF) sensor. Then, the control unit 561 calculates the distance d on the basis of the endoscopic image captured by the range image sensor.

After Step S1C, the control unit 561 calculates a scanning speed V (FIG. 3) according to the movement of the optical fiber 51 relative to the urinary calculus ST when the insertion section 21 is moved by the operator (Step S1D).

Specifically, as a calculation method for calculating the scanning speed V, any one of the following methods (4) to (6) can be adopted.

(4) Calculation Method for Calculating Scanning Speed V Based on Endoscopic Image The control unit 561 calculates the scanning speed V basis of the endoscopic image obtained by imaging the urinary calculus ST.

Specifically, for example, the imaging device 22 includes a stereo camera. Here, the control unit 561 uses the stereo measurement technology in which a relative displacement in images of the same object that are imaged at the same time from different viewpoints by the stereo camera to calculate a three-dimensional position of the object on the basis of the principle of the triangulation. Then, the control unit 561 divides an amount of movement between the three-dimensional positions of specific positions having high correlation between adjacent frames (endoscopic images) arranged in time series by a time between the adjacent frames, and calculates the scanning speed V.

Furthermore, for example, the control unit 561 estimates an optical flow between adjacent frames arranged in time series to calculate the scanning speed V.

(5) Calculation Method for Calculating Scanning Speed V Based on Speckle Pattern Incidentally, when the guide light is applied to the urinary calculus ST, light scattered on the surface of the urinary calculus ST interferes with each other, and a random spot pattern called a speckle pattern is formed.

Then, the control unit 561 uses the speckle pattern of the feedback light detected by the light detector 55 to calculate an amount of movement of the speckle pattern caused by the movement of the optical fiber 51 relative to the urinary calculus ST, and the scanning speed V is calculated.

(6) Calculation Method for Calculating Scanning Speed Using Doppler Effect

The control unit 561 calculates the scanning speed V on the basis of a change between a wavelength of the guide light emitted from the guide light source 522 and a wavelength of the feedback light detected by the light detector 55. In other words, the control unit 561 calculates the scanning speed V by using the so-called Doppler effect.

After Step S1D, the control unit 561 calculates an overlap index value I indicating an overlap area ArO (FIG. 3) in an irradiation area irradiated with the surgical laser light, according to the movement of the optical fiber 51 relative to the urinary calculus ST upon movement of the insertion section 21 by the operator (Step S1E). The overlap index value I corresponds to "overlap information that is information about the overlap area".

Here, as illustrated in FIG. 3, the overlap area ArO means an area where an irradiation area Ar1 irradiated with the surgical laser light applied to the urinary calculus ST by the first pulse emission of the surgical laser light and an irradiation area Ar2 irradiated with the surgical laser light applied to the urinary calculus ST in the second pulse emission overlap each other.

Incidentally, the following factor can be considered as the factors of a flashing phenomenon.

Application of the surgical laser light to the urinary calculus ST by the first pulse emission, the surface of the urinary calculus ST corresponding to the irradiation area Ar1 is crushed. At this time, as illustrated in FIG. 3, a crush failure portion ST1 having heat but being not fractured may remain in the irradiation area Ar1. Then, when the surgical laser light applied to the crush failure portion ST1 by the second pulse emission reheats the crush failure portion ST1, the flashing phenomenon occurs due to black body radiation caused by heat accumulated in the crush failure portion ST1.

In consideration of the factor described above, the disclosure focuses on the overlap area ArO in order to suppress the flashing phenomenon.

Specifically, in Step S1E, the control unit 561 calculates, as the overlap index value I, W/L obtained by dividing the diameter W (FIG. 3) of each of the irradiation areas Ar1 and Ar2 by a movement distance L (FIG. 3) through which the optical fiber 51 is moved per pulse of the surgical laser light.

Here, the control unit 561 calculates, as the diameter W, $(D+2d \tan \theta)$ on the basis of the distance d that has been calculated in Step S1C, and the fiber diameter D, the numerical aperture NA, and the refractive index n that have been stored in the storage unit 562. Note that $\theta$ can be derived from $NA = n \sin \theta$.

Furthermore, the control unit 561 calculates, as the movement distance L, V/f obtained by dividing the scanning speed V having been calculated in Step S1D by the pulse frequency f having been stored in the storage unit 562.

After Step S1E, the control unit 561 determines whether the overlap index value I having been calculated in Step S1E satisfies a specific condition (Step S1F).

In the present first embodiment, whether to satisfy the specific condition means whether to satisfy a relationship I<N+1.

Here, N is the number of times of overlapping (hereinafter, described as overlapping frequency) of the irradiation areas on the urinary calculus ST irradiated with the surgical laser light upon emission of each pulse, during the pulse emission of the surgical laser light. For example, when N is 0, the above-described condition is a condition that there is no overlap, that is, the overlap area ArO is 0. Note that the N may have a preset value, or may have a value set according to the user operation to the input unit 563 by the operator or the like.

When it is determined that the overlap index value I satisfies the specific condition (Step S1F: Yes), the control unit 561 returns to Step S1C. For example, when N is 0, the control unit 561 determines that the overlap index value I is smaller than 1 and there is not the overlap area ArO (Step S1F: Yes), and returns to Step S1C and continues (permits) the emission of the laser light.

On the other hand, when it is determined that the overlap index value I does not satisfy the specific condition (Step S1F: No), the control unit 561 stops the operation of the surgical laser light source 521 (Step S1G). Therefore, crushing of the urinary calculus ST is stopped.

According to the present first embodiment described above, the following effects are obtained.

The control unit 561 constituting the control device 56 according to the present first embodiment calculates the overlap index value I indicating the overlap area ArO in an irradiation area irradiated with the surgical laser light, according to the movement of the optical fiber 51 relative to the urinary calculus ST. Then, the control unit 561 controls the output of the surgical laser light from the surgical laser light source 521, on the basis of the overlap index value I. In other words, the control unit 561 controls the output of the surgical laser light from the surgical laser light source 521 in consideration of the overlap area ArO considered as the factor causing the flashing phenomenon.

Therefore, the control device 56 according to the present first embodiment is configured to suppress the occurrence of the flashing phenomenon. As a result, the operator is less likely to interrupt the manipulation in response to the flashing phenomenon. In addition, the surgical duration can be reduced, and the fatigue of the operator can also be reduced.

In particular, the control unit 561 calculates the distance d and the scanning speed V to calculate the overlap index value I, on the basis of the distance d and the scanning speed V.

This configuration makes it possible to accurately calculate the overlap index value I to effectively suppress the occurrence of the flashing phenomenon.

Second Embodiment

Next, a second embodiment will be described.

In the following description, configurations similar to those of the first embodiment described above are denoted by the same reference signs, and detailed description thereof is omitted or simplified.

Figure 4:
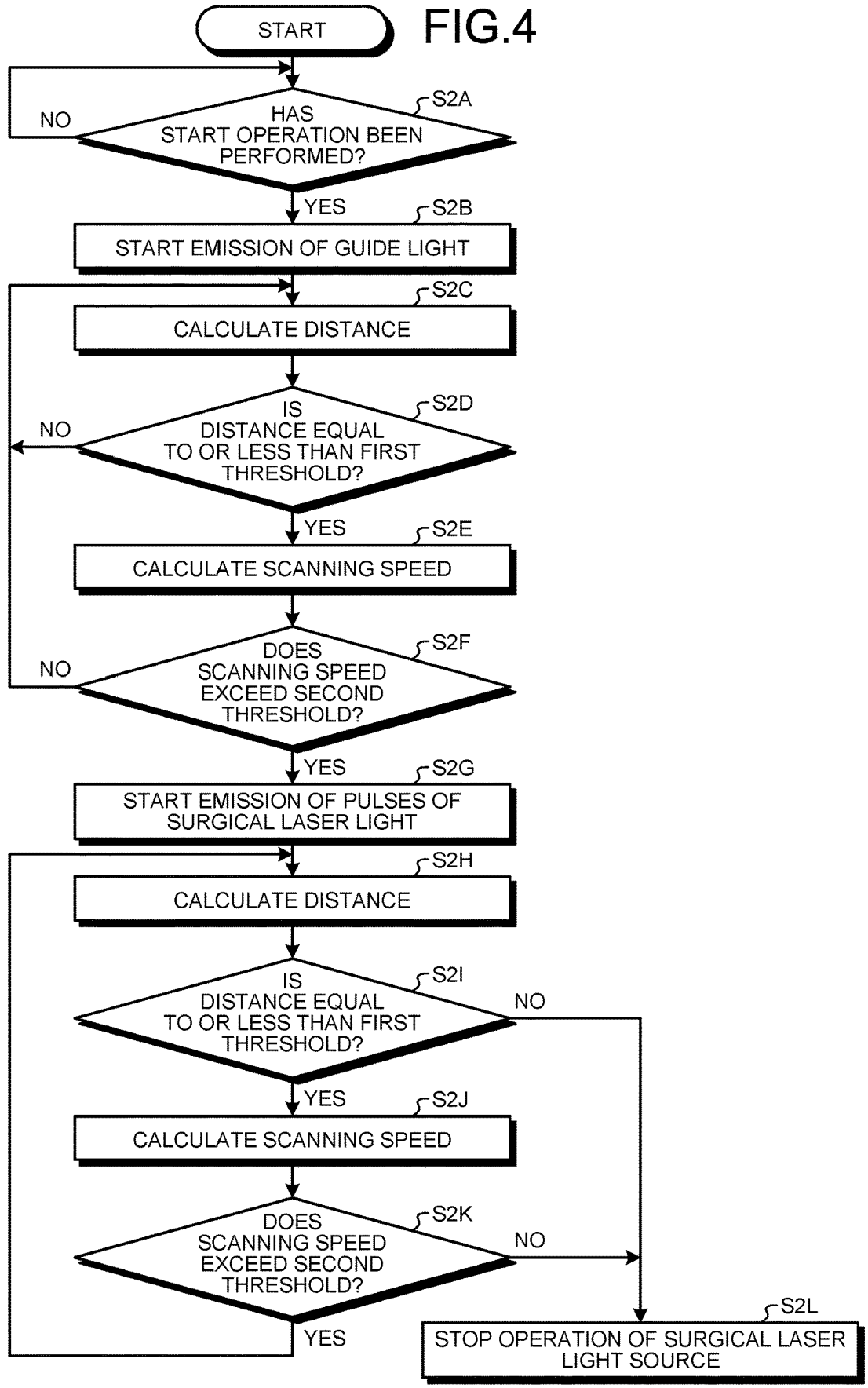
FIG. 4 is a flowchart illustrating a control method according to a second embodiment.

FIG. 4 is a flowchart illustrating a control method according to the second embodiment.

As illustrated in FIG. 4, the present second embodiment is different from the first embodiment in the control method executed by the control device 56.

The control method according to the present second embodiment will be described below with reference to FIG. 4.

First, as in Step S1A described in the above first embodiment, the control unit 561 constantly monitors whether the start operation is input to the foot switch 4 by the operator (Step S2A).

Then, when it is determined that the start operation has been input (Step S2A: Yes), the control unit 561 controls the operation of the light source device 52 to start emission of the guide light from the guide light source 522 (Step S2B).

After Step S2B, the control unit 561 calculates the distance d as in Step S1C described in the above first embodiment (Step S2C).

After Step S2C, the control unit 561 determines whether the distance d calculated in Step S2C is equal to or less than a first threshold (Step S2D).

Here, the first threshold may have a preset value, or may have a value set according to the user operation to the input unit 563 by the operator or the like.

When it is determined that the distance d exceeds the first threshold (Step S2D: No), the control unit 561 returns to Step S2C.

When it is determined that the distance d is equal to or less than the first threshold (Step S2D: Yes), the control unit 561 calculates the scanning speed V as in Step S1D described in the above first embodiment (Step S2E).

After Step S2E, the control unit 561 determines whether the scanning speed V calculated in Step S2E exceeds a second threshold (Step S2F).

Here, as the second threshold value, a value can be adopted that is calculated from $(D+2d \tan \theta) \cdot f/(N+1)$, on the basis of the distance d that has been calculated in Step S2C, and the fiber diameter D, the numerical aperture NA, the refractive index n, and the pulse frequency f that have been stored in the storage unit 562, and the overlapping frequency N. Note that $\theta$ can be derived from $NA = n \sin \theta$.

When it is determined that the scanning speed V is equal to or less than the second threshold (Step S2F: No), the control unit 561 returns to Step S2C.

When it is determined that the scanning speed V exceeds the second threshold value (Step S2F: Yes), the control unit 561 controls the operation of the light source device 52 to cause the surgical laser light source 521 to start emission of pulses of the surgical laser light (Step S2G).

After Step S2G, the control unit 561 calculates the distance d as in Step S2C (Step S2H), and then, determines whether the distance d is equal to or less than the first threshold as in Step S2D (Step S2I).

When it is determined that the distance d exceeds the first threshold (Step S2I: No), the control unit 561 proceeds to Step S2L.

On the other hand, when it is determined that the distance d is equal to or less than the first threshold (Step S2I: Yes), the control unit 561 calculates the scanning speed V as in Step S2E (Step S2J), and then, determines whether the scanning speed V exceeds the second threshold as in Step S2F (Step S2K).

When it is determined that the scanning speed V exceeds the second threshold (Step S2K: Yes), the control unit 561 returns to Step S2I.

On the other hand, when it is determined that the scanning speed V is equal to or less than the second threshold (Step S2K: No) or when it is determined that the distance d exceeds the first threshold (Step S2I: No), the control unit

561 stops the operation of the surgical laser light source 521 (Step S2L) as in Step S1G described in the above first embodiment.

According to the present second embodiment described above, the following effects are obtained.

The control unit 561 according to the present second embodiment calculates the scanning speed V according to the movement of the optical fiber 51 relative to the urinary calculus ST. Then, the control unit 561 controls the output of the surgical laser light from the surgical laser light source 521, on the basis of the scanning speed V. In other words, the control unit 561 controls the output of the surgical laser light from the surgical laser light source 521, in consideration of the scanning speed V caused by the overlap area ArO considered as the factor causing the flashing phenomenon.

Therefore, the control device 56 according to the present second embodiment is configured to suppress the occurrence of the flashing phenomenon. As a result, the operator is less likely to interrupt the manipulation in response to the flashing phenomenon. In addition, the surgical duration can be reduced, and the fatigue of the operator can also be reduced.

In addition, the control unit 561 according to the present second embodiment controls the output of the surgical laser light from the surgical laser light source 521, in consideration of the distance d caused by the overlap area ArO as well, in addition to the scanning speed V.

This configuration makes it possible to effectively suppress the occurrence of the flashing phenomenon.

In particular, only when conditions for emission of the surgical laser light are satisfied (Step S2D: Yes, Step S2F: Yes), the emission of pulses of the surgical laser light is started (Step S2G), and therefore, the emission of pulses can be started at an appropriate timing. This configuration makes it possible to effectively suppress the occurrence of the flashing phenomenon to efficiently crush the urinary calculus ST.

Third Embodiment

Next, a third embodiment will be described.

In the following description, configurations similar to those of the first embodiment described above are denoted by the same reference signs, and detailed description thereof is omitted or simplified.

Figure 5:
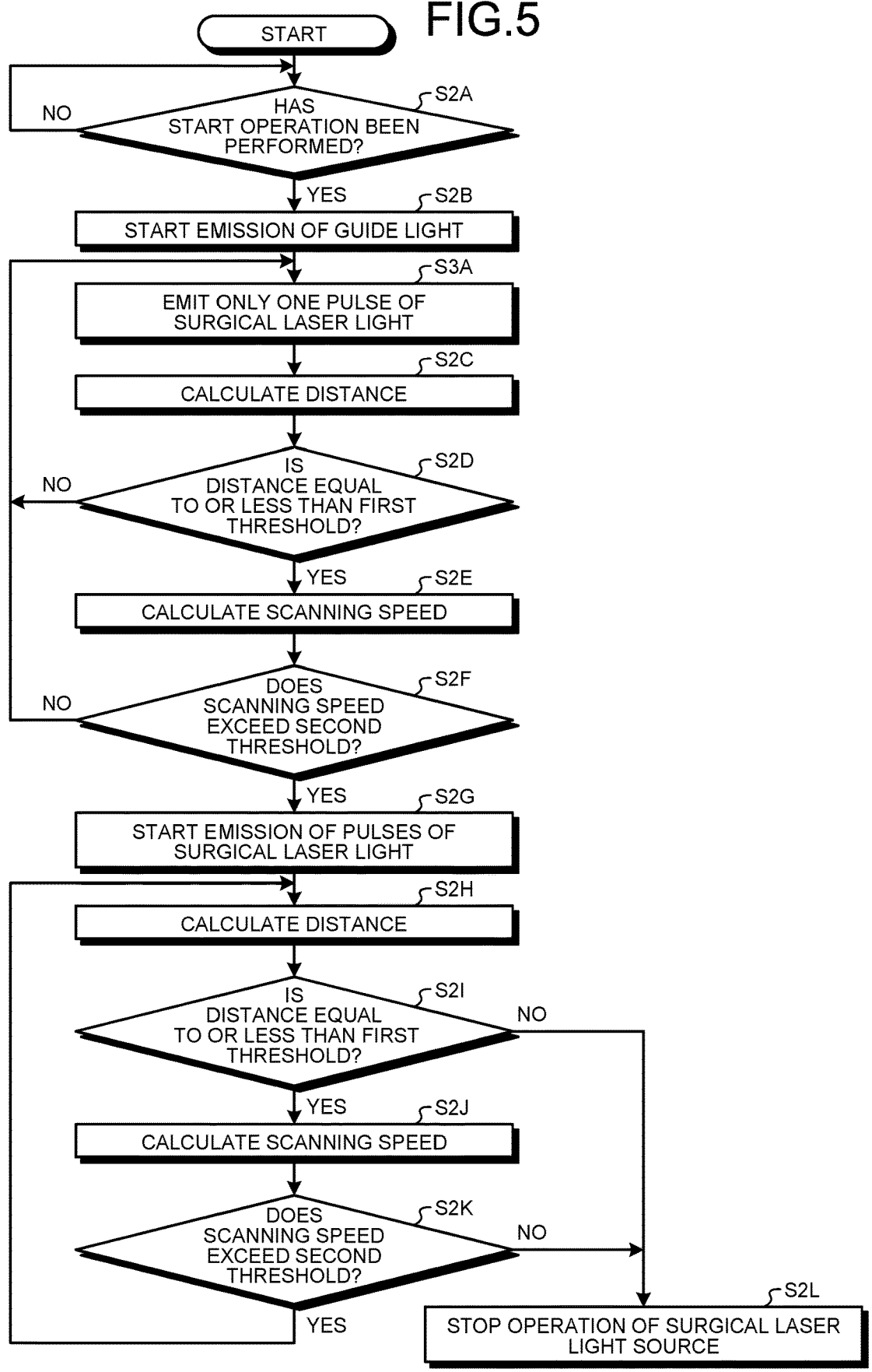
FIG. 5 is a flowchart illustrating a control method according to a third embodiment.

FIG. 5 is a flowchart illustrating a control method according to the third embodiment.

As illustrated in FIG. 5, the present third embodiment is different from the first and second embodiments in the control method executed by the control device 56.

The control method according to the present third embodiment will be described below with reference to FIG. 5.

As illustrated in FIG. 5, the control method according to the present third embodiment is different from the control method described in the above second embodiment in that Step S3A is added. Therefore, only Step S3A will be mainly described below.

Step S3A is performed after Step S2B.

Specifically, in Step S3A, the control unit 561 controls the operation of the light source device 52 to cause the surgical laser light source 521 to emit only one pulse of the surgical laser light. Then, the control unit 561 proceeds to Step S2C.

Note that when it is determined that the distance d exceeds the first threshold (Step S2D: No) and when it is determined that the scanning speed V is equal to or less than the second threshold (Step S2F: No), the control unit 561 returns to Step S3A.

According to the present third embodiment described above, the effects similar to those of the second embodiment described above are obtained.

Before satisfying the conditions for emission of the surgical laser light (Step S2D: Yes, Step S2F: Yes), the control unit 561 according to the present third embodiment emits only one pulse of the surgical laser light (Step S3A).

Therefore, the surface of the urinary calculus ST is partially crushed by the application of only one pulse of the surgical laser light to the urinary calculus ST, and therefore, the operator can clearly recognize the timing at which the insertion section 21 (optical fiber 51) may be moved, from the endoscopic image displayed on the display device 3. In addition, partial crushing of the surface of the urinary calculus ST prevents the distal end of the optical fiber 51 from being caught on the surface of the urinary calculus ST when the optical fiber 51 is moved, making the operator readily move the insertion section 21 (optical fiber 51).

Fourth Embodiment

Next, a fourth embodiment will be described.

In the following description, configurations similar to those of the first embodiment described above are denoted by the same reference signs, and detailed description thereof is omitted or simplified.

Figure 6:
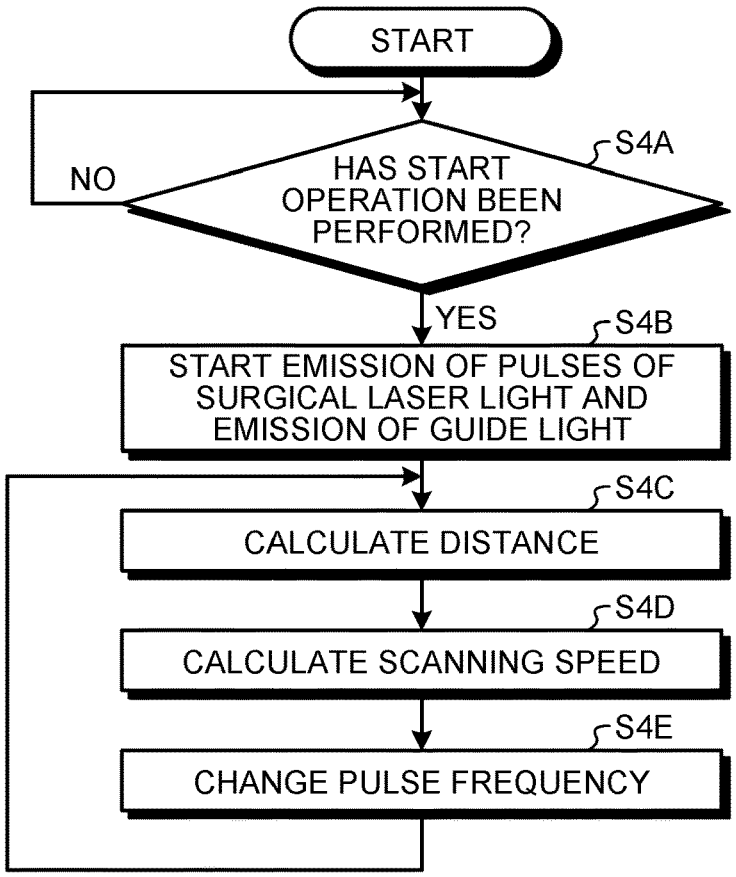
FIG. 6 is a flowchart illustrating a control method according to a fourth embodiment.

FIG. 6 is a flowchart illustrating a control method according to the fourth embodiment.

As illustrated in FIG. 6, the present fourth embodiment is different from the first to third embodiments in the control method executed by the control device 56.

The control method according to the present fourth embodiment will be described below with reference to FIG. 6.

First, as in Step S1A described in the above first embodiment, the control unit 561 constantly monitors whether the start operation is input to the foot switch 4 by the operator (Step S4A).

Then, when it is determined that the start operation has been input (Step S4A: Yes), the control unit 561 controls the operation of the light source device 52 to cause the surgical laser light source 521 to start emission of pulses of the surgical laser light and cause the guide light source 522 to start emission of the guide light (Step S4B).

After Step S4B, the control unit 561 calculates the distance d as in Step S1C described in the above first embodiment (Step S4C), and then, calculates the scanning speed V as in Step S1D described in the above first embodiment (Step S4D).

After Step S4D, the control unit 561 controls the operation of the surgical laser light source 521 on the basis of pulse frequency change information stored in the storage unit 562, the distance d calculated in Step S4C, and the scanning speed V calculated in Step S4D, and changes the pulse frequency f of pulses of the surgical laser light emitted (Step S4E). Then, the control unit 561 returns to Step S4C.

Figure 7:
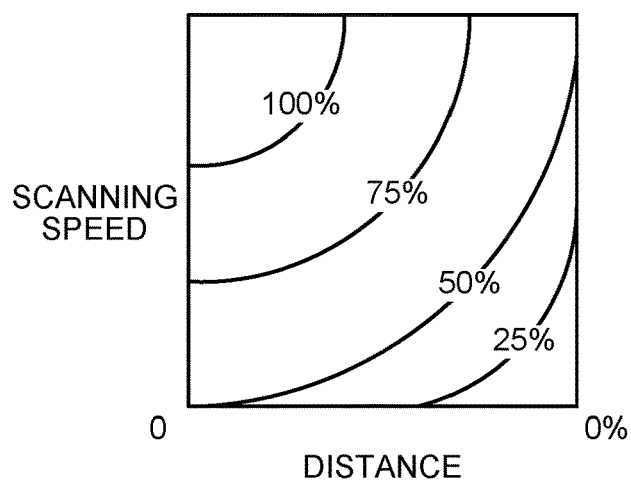
FIG. 7 is a graph illustrating pulse frequency change information.

FIG. 7 is a graph illustrating the pulse frequency change information. Here, in FIG. 7, the horizontal axis represents the distance d. The vertical axis represents the scanning speed V. Furthermore, the changed pulse frequency f is expressed in %.

The pulse frequency change information is information in which the changed pulse frequency f is associated with a combination of the distance d calculated in Step S4C and the scanning speed V calculated in Step S4D.

Here, in the present fourth embodiment, the pulse frequency change information is set so that the pulse frequency f decreases as the scanning speed V decreases. Furthermore, the pulse frequency change information is set so that the pulse frequency f decreases as the distance d increases.

In the example of FIG. 7, in an upper left area where the distance d is small and the scanning speed V is high, the changed pulse frequency f is set to "100%." Note that "100%" means that, for example, the pulse frequency f (hereinafter, described as a set value f0) stored in the storage unit 562 and set according to the user operation to the input unit 563 by the operator or the like is used as the changed pulse frequency f. Then, as the distance d becomes larger and the scanning speed V becomes lower, in other words, the changed pulse frequency f is sequentially changed to "75%," "50%," "25%," and "0%," toward a lower right side of FIG. 7. Note that "75%" means that a value of 75% of the set value f0 is used as the pulse frequency f. Furthermore, "50%" means that a value of 50% of the set value f0 is used as the pulse frequency f. Furthermore, "25%" means that a value of 25% of the set value f0 is used as the pulse frequency f. In addition, "0%" means to stop the operation of the surgical laser light source 521.

According to the present fourth embodiment described above, the following effects are obtained.

The control unit 561 according to the present fourth embodiment calculates the scanning speed V according to the movement of the optical fiber 51 relative to the urinary calculus ST. Then, the control unit 561 changes the pulse frequency f on the basis of the scanning speed V. In other words, the control unit 561 changes the pulse frequency f in consideration of the scanning speed V caused by the overlap area ArO considered as the factor causing the flashing phenomenon to adjust the overlap area ArO.

Therefore, the control device 56 according to the present fourth embodiment is configured to suppress the occurrence of the flashing phenomenon. As a result, the operator is less likely to interrupt the manipulation in response to the flashing phenomenon. In addition, the surgical duration can be reduced, and the fatigue of the operator can also be reduced.

Furthermore, the control unit 561 according to the present fourth embodiment changes the pulse frequency f in consideration of the distance d caused by the overlap area ArO as well, in addition to the scanning speed V.

This configuration makes it possible to effectively suppress the occurrence of the flashing phenomenon.

Modification 4-1

Figure 8:
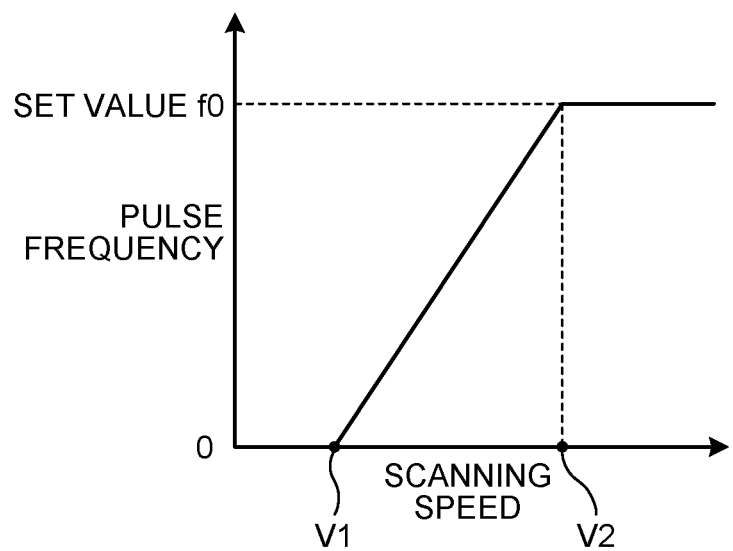
FIG. 8 is a graph illustrating a modification 4-1 of the fourth embodiment.

FIG. 8 is a graph illustrating a modification 4-1 of the fourth embodiment. Specifically, FIG. 8 is the graph illustrating pulse frequency change information according to the present modification 4-1. Here, in FIG. 8, the horizontal axis represents the scanning speed V. The vertical axis represents the pulse frequency f.

In Step S4E according to the above fourth embodiment, the control unit 561 has changed the pulse frequency f on the basis of the pulse frequency change information stored in the storage unit 562, the distance d calculated in Step S4C, and the scanning speed V calculated in Step S4D. However, the method of changing the pulse frequency f is not limited thereto.

For example, the control unit 561 may not execute Step S4C, but may change, in Step S4E, the pulse frequency f on the basis of the pulse frequency change information stored in the storage unit 562 and the scanning speed V calculated in Step S4D.

The pulse frequency change information according to the present modification 4-1 is information in which the changed pulse frequency f is associated with the scanning speed V calculated in Step S4D, and the pulse frequency change information is set so that the pulse frequency f decreases as the scanning speed V decreases.

Specifically, as illustrated in FIG. 8, the pulse frequency change information is set so that the pulse frequency f reaches "0" within the range of the scanning speed V from 0 to a scanning speed V1. In other words, in this range, the operation of the surgical laser light source 521 is stopped. Furthermore, the pulse frequency change information is set so that the pulse frequency f increases from "0" as the scanning speed V increases from the scanning speed V1. Furthermore, the pulse frequency change information is set so that the pulse frequency f reaches the set value f0 when the scanning speed V is equal to or higher than a scanning speed V2.

Modification 4-2

Figure 9:
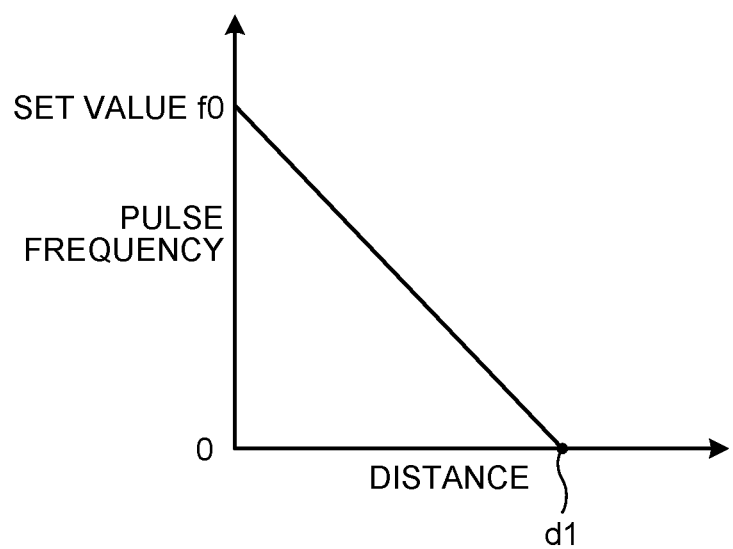
FIG. 9 is a graph illustrating a modification 4-2 of the fourth embodiment.

FIG. 9 is a graph illustrating a modification 4-2 of the fourth embodiment. Specifically, FIG. 9 is the graph illustrating pulse frequency change information according to the present modification 4-2. Here, in FIG. 9, the horizontal axis represents the distance d. The vertical axis represents the pulse frequency f.

In Step S4E according to the above fourth embodiment, the control unit 561 has changed the pulse frequency f on the basis of the pulse frequency change information stored in the storage unit 562, the distance d calculated in Step S4C, and the scanning speed V calculated in Step S4D. However, the method of changing the pulse frequency f is not limited thereto.

For example, the control unit 561 may not execute Step S4D, but may change, in Step S4E, the pulse frequency f on the basis of the pulse frequency change information stored in the storage unit 562 and the distance d calculated in Step S4C.

The pulse frequency change information according to the preset modification 4-2 is information in which the changed pulse frequency f is associated with the distance d calculated in Step S4C, and is set so that the pulse frequency f decreases as the distance d increases.

Specifically, as illustrated in FIG. 9, the pulse frequency change information is set so that the pulse frequency f is the set value f0 when the distance d is "0." Furthermore, the pulse frequency change information is set so that the pulse frequency f decreases from the set value f0 as the distance d increases from "0." Furthermore, the pulse frequency change information is set so that the pulse frequency f reaches "0" when the distance d is equal to or larger than a distance dl. In other words, when the distance d is equal to or larger than the distance dl, the operation of the surgical laser light source 521 is stopped.

Fifth Embodiment

Next, a fifth embodiment will be described.

In the following description, configurations similar to those of the first embodiment described above are denoted by the same reference signs, and detailed description thereof is omitted or simplified.

Figure 10:
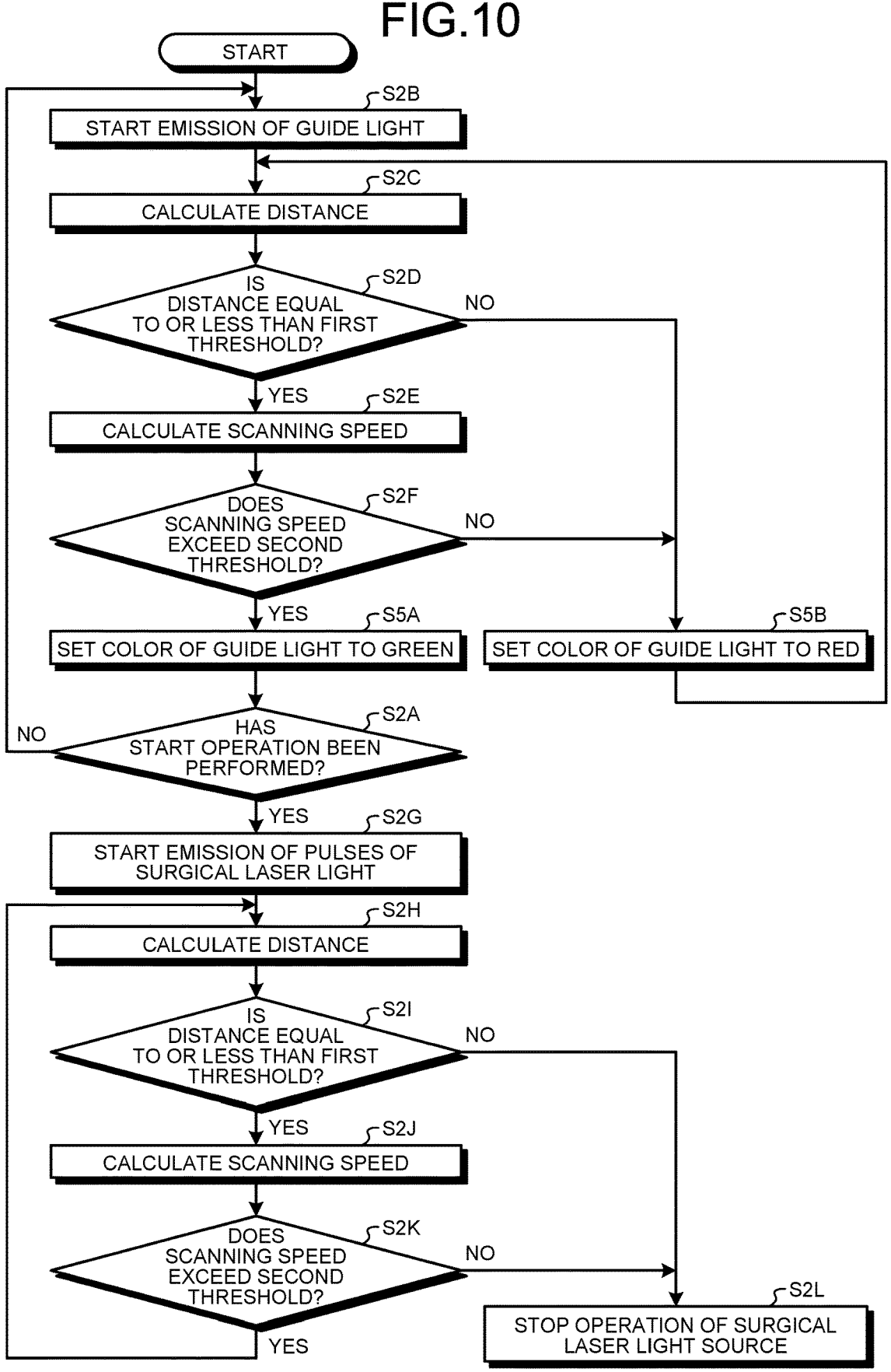
FIG. 10 is a flowchart illustrating a control method according to a fifth embodiment.

FIG. 10 is a flowchart illustrating a control method according to the fifth embodiment.

As illustrated in FIG. 10, the present fifth embodiment is different from the first to fourth embodiments in the control method executed by the control device 56.

The control method according to the present fifth embodiment will be described below with reference to FIG. 10.

As illustrated in FIG. 10, the control method according to the present fifth embodiment is different from the control method described in the above second embodiment in that the execution timing of Step S2A is different and Steps S5A and S5B are added. Therefore, only Steps S5A, S5B, and S2A will be mainly described below.

Step S5A is performed when it is determined that the scanning speed V exceeds the second threshold (Step S2F: Yes).

Specifically, in Step S5A, the control unit 561 controls the operation of the guide light source 522 to set the color of the guide light emitted from the guide light source 522 to green. Therefore, the operator recognizes that the color of the guide light is set to green and the surgical laser light can be emitted, from the endoscopic image displayed on the display device 3.

Note that in Step S2B, the color of the guide light emitted from the guide light source 522 is a color other than green (also including red).

Then, after Step S5A, Step S2A is performed.

When it is determined that the start operation has been input (Step S2A: Yes), the control unit 561 proceeds to Step S2G.

On the other hand, when it is determined that no start operation is input (Step S2A: No), the control unit 561 returns to Step S2C.

Step S5B is performed when it is determined that the distance d exceeds the first threshold (Step S2D: No) or when it is determined that the scanning speed V is equal to or less than the second threshold (Step S2F: No).

Specifically, in Step S5B, the control unit 561 controls the operation of the guide light source 522 to set the color of the guide light emitted from the guide light source 522 to red. Therefore, the operator recognizes that the color of the guide light is set to red and the surgical laser light should not be emitted, from the endoscopic image displayed on the display device 3.

Then, after Step S5B, the control unit 561 returns to Step S2C.

According to the modification of the present fifth embodiment described above, the following effects, in addition to the effects similar to those of the second embodiment described above are obtained.

When the conditions for emission of the surgical laser light are satisfied (Step S2D: Yes, Step S2F: Yes), the control unit 561 according to the present fifth embodiment sets the color of the guide light to green (Step S5A).

Therefore, the operator can clearly recognize that the conditions for emission of the surgical laser light are satisfied, from the endoscopic image displayed on the display device 3, and can start the emission of pulses of the surgical laser light.

In the fifth embodiment described above, setting the color of the guide light to green in Step S5A notifies the operator of satisfaction of the conditions for emission of the surgical laser light, but the disclosure is not limited thereto.

For example, in Step S5A, the guide light may be blinked to notify the operator of the satisfaction of the conditions for emission of the surgical laser light.

In addition, for example, in Step S5A, a specific message or the like may be displayed on the display device 3 to notify the operator of the satisfaction of the conditions for emission of the surgical laser light.

Furthermore, for example, in Step S5A, sound may be output from a speaker to notify the operator of the satisfaction of the conditions for emission of the surgical laser light.

OTHER EMBODIMENTS

The embodiments for carrying out the disclosure have been described above, but it should be understood that the disclosure is not limited only to the above first to fifth embodiments and modifications 4-1 and 4-2.

In the above first to third embodiments and the fifth embodiment, a configuration may be adopted in which the process returns to Step S1B (Step S2G) after a predetermined time has passed after Step S1G (Step S2L).

In the above first to fifth embodiments and modifications 4-1 and 4-2, in a case where the operator operates the distal end of the optical fiber 51 to abut on the urinary calculus ST as manipulation for crushing the urinary calculus ST, the distance d is always 0, and thus Step S1C (Steps S2C, S2D, S2H, S2I, and S4C) are unnecessary.

According to the control device and the control method according to the disclosure, it is possible to suppress a flashing phenomenon that occurs during crushing of a calculus.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device, comprising:
  a processor including hardware, the processor being configured to:
    control a laser light source to emit a first instance of a laser light,
    calculate an overlap information related to an overlap area of an irradiation area of an irradiation target that is irradiated with the first instance of the laser light, and
    control the laser light source to emit a second instance of the laser light based on the overlap information.

2. The control device according to claim 1, wherein the processor is further configured to calculate an overlap index value, and
  wherein the overlap index includes an overlap information based on a diameter of the irradiation area and on a movement distance of the laser light source.

3. The control device according to claim 2, wherein the processor is further configured to calculate the movement distance based on a rate of movement of the light source and on a pulse frequency of the emitted laser light.

4. The control device according to claim 2, wherein the processor is further configured to calculate the diameter of the irradiation area based on:
  a distance between the irradiation area and the laser light source,
  a diameter of an optical fiber of the laser light source,
  a numerical aperture of the optical fiber, and
  a refractive index of a medium through which the emitted laser light passes.

5. The control device according to claim 2, wherein the processor is further configured to:
  determine a presence or an absence of the overlap area based on the overlap index value, and
  permit emission of the laser light when the overlap area is determined to be absent.

6. The control device according to claim 3, wherein the scanning speed is further based on an endoscopic image obtained by imaging the irradiation area.

7. The control device according to claim 3, wherein the scanning speed is further based on a speckle pattern formed by light that is applied to the irradiation area and an amount that is scattered by the irradiation are.

8. The control device according to claim 3, wherein the processor is further configured to calculate the scanning speed by using a Doppler effect based on light that is applied to the irradiation area and that is reflected and returned from the irradiation area.

9. The control device according to claim 4, wherein the processor is further configured to calculate the distance based on a brightness of light applied to the irradiation area and that is reflected by the irradiation area.

10. The control device according to claim 4, wherein the processor is further configured to calculate the distance based on a time from application of light to the irradiation area to reflecting and returning of light from the irradiation area.

11. The control device according to claim 4, wherein the processor is further configured to calculate the distance based on an endoscopic image obtained by imaging the irradiation area.

12. The control device according to claim 3, wherein the processor is further configured to reduce the pulse frequency as the scanning speed decreases.

13. The control device according to claim 4, wherein the processor is further configured to reduce a pulse frequency of the emitted laser light as the distance increases.

14. A control device, comprising:
  a processor including hardware, the processor being configured to:
    control operation of a laser light source to cause the laser light source to emit a pulse of laser light and to apply the laser light to an irradiation target through an optical fiber,
    calculate a scanning speed according to a movement of the optical fiber relative to the irradiation target, and
    control an output of the laser light from the laser light source based on the scanning speed.

15. The control device according to claim 14, wherein the output is a pulse frequency of the pulses of the laser light, and
  wherein the processor is further configured to reduce the pulse frequency as the scanning speed decreases.

16. The control device according to claim 14, wherein the processor is further configured to calculate a distance between the irradiation area and the optical fiber, and
  wherein the output of the laser light from the laser light source is controlled based on the scanning speed and on the distance.

17. The control device according to claim 16, wherein the output is a pulse frequency of the pulses of the laser light, and
  wherein the processor is further configured to reduce the pulse frequency as the distance increases.

18. The control device according to claim 1, wherein the irradiation area of the irradiation target that is irradiated with the first instance of the laser light is a first irradiation area,
  wherein an irradiation area of an irradiation target that is irradiated with the second instance of the laser light is a second irradiation area, and
  wherein the overlap area is an area where the first irradiation area and the second irradiation area overlap each other.

19. A control method executed by a processor of a control device, the control method comprising:
  calculating an overlap information related to an overlap area of a first irradiation area of an irradiation target that is irradiated with a first instance of a laser light emitted from a laser light source, and
  controlling the laser light source to emit a second instance of the laser light based on the overlap information.

20. The control method according to claim 19, wherein an irradiation area of an irradiation target that is irradiated with the second instance of the laser light is a second irradiation area, and
  wherein the overlap area is an area where the first irradiation area and the second irradiation area overlap each other.

* * * * *